United States Patent [19]

Frost et al.

[11] Patent Number: 5,663,183
[45] Date of Patent: Sep. 2, 1997

[54] N-(3-AMINOPROPYL)-N-PHENYL-5,6,7,8-TETRAHYDRONAPHTHALENE-2-CARBOXAMIDE DERIVATIVES, THEIR PREPARATION AND THEIR THERAPEUTIC USE

[75] Inventors: Jonathan Frost, Wissous; Pascal George, St Arnoult en Yvelines; Patrick Pasau, Bagneux; Régine Bartsch; Corinne Rousselle, both of Fontenay aux Roses; Paul Howard Williams, Paris; Jean Claude Muller, Morsang sur Orge, all of France

[73] Assignee: Synthelabo, Le Plessis Robinson, France

[21] Appl. No.: 653,233

[22] Filed: May 24, 1996

Related U.S. Application Data

[63] Continuation of Ser. No. 382,578, Feb. 2, 1995, Pat. No. 5,550,162.

[30] Foreign Application Priority Data

| Feb. 3, 1994 | [FR] | France | 94.01198 |
| Feb. 3, 1994 | [FR] | France | 94.01199 |
| Feb. 3, 1994 | [FR] | France | 94.01200 |

[51] Int. Cl.$^6$ .............. A61K 31/47; C07D 217/00
[52] U.S. Cl. .............. 514/310; 514/213; 514/292; 514/301; 514/415; 514/419; 540/594; 546/85; 546/87; 546/114; 546/143; 548/469; 548/490
[58] Field of Search .............. 514/213, 292, 514/301, 310, 415, 419; 540/594; 546/85, 87, 114, 143; 548/469, 490

[56] References Cited

U.S. PATENT DOCUMENTS

| 3,483,206 | 12/1969 | Werner | 546/146 |
| 4,584,293 | 4/1986 | Reiffen et al. | 514/213 |
| 5,001,159 | 3/1991 | Hoornaert et al. | 514/619 |
| 5,075,325 | 12/1991 | Hoornaert et al. | 514/357 |
| 5,137,901 | 8/1992 | Junge et al. | 514/373 |
| 5,300,523 | 4/1994 | Junge et al. | 514/456 |
| 5,373,023 | 12/1994 | William et al. | 514/617 |
| 5,382,595 | 1/1995 | Minami et al. | 514/617 |

FOREIGN PATENT DOCUMENTS

| 0 233 762 | 2/1987 | European Pat. Off. . | |
| 3 202 100 | 8/1983 | Germany | 564/180 |
| 3 405 329 | 8/1985 | Germany | 564/180 |

*Primary Examiner*—Shailendra Kumar
*Attorney, Agent, or Firm*—Jacobson, Price, Holman & Stern, PLLC

[57] ABSTRACT

Compounds of the formula:

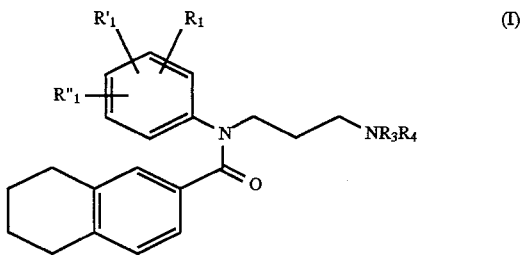

in which $R_1$ represents a hydrogen or halogen atom or a methyl or $C_1$–$C_4$ alkoxy group, $R'_1$ represents a hydrogen or halogen atom, $R''_1$ represents a hydrogen atom or a methoxy group, $R_3$ represents a $C_1$–$C_3$ alkyl group, $R_4$ represents a 2,3-dihydro-1H-inden-2-yl, 2,3-dihydro-1H-inden-1-yl or 1,2,3,4-tetrahydronaphthalen-1-yl group, or $R_3$ and $R_4$ together form, with the adjacent nitrogen atom, a 1,2,3,4-tetrahydroisoquinol-2-yl, 6,7-dimethoxy-1,2,3,4-tetrahydroisoquinol-2-yl, 5,8-dimethoxy-1,2,3,4-tetrahydroisoquinol-2-yl, 1,2,3,4-tetrahydro-9H-pyrido[3,4-b]indol-2-yl, 1,2,3,4-tetrahydro-9H-pyrido[4,3-b]indol-3-yl, 4,5,6,7-tetrahydrothieno[2,3-c]pyrid-6-yl, 2,3-dihydro-1H-isoindol-2-yl or 2,3,4,5-tetra-hydro-1H-3-benzazepin-3-yl, group are useful in the treatment of cerebral disorders.

3 Claims, No Drawings

N-(3-AMINOPROPYL)-N-PHENYL-5,6,7,8-TETRAHYDRONAPHTHALENE-2-CARBOXAMIDE DERIVATIVES, THEIR PREPARATION AND THEIR THERAPEUTIC USE

This is a continuation of application Ser. No. 08/382,578, filed Feb. 2, 1995, now U.S. Pat. No. 5,550,162.

The present invention relates to N-(3-aminopropyl)-N-phenyl-5,6,7,8-tetrahydronaphthalene-2-carboxamide derivatives, to their preparation and to their therapeutic use.

The invention provides the compounds of the general formula (I)

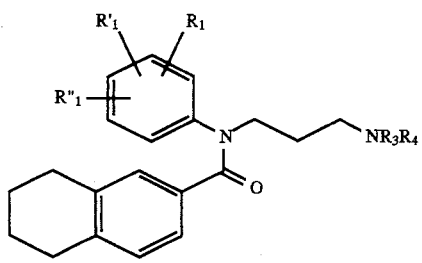

in which $R_1$ represents a hydrogen or halogen atom, a methyl group or a $C_1$–$C_4$ alkoxy group, $R'_1$ represents a hydrogen or halogen atom, $R''_1$ represents a hydrogen atom or a methoxy group, $R_3$, taken alone, represents a $C_1$–$C_3$ alkyl group, $R_4$, taken alone, represents a 2,3-dihydro-1H-inden-2-yl group, a 2,3-dihydro-1H-inden-1-yl group or a 1,2,3,4-tetrahydronaphthalen-1-yl group, or alternatively $R_3$ and $R_4$ together form, with the nitrogen atom to which they are attached, a 1,2,3,4-tetrahydroisoquinol-2-yl group, a 6,7-dimethoxy-1,2,3,4-tetrahydroisoquinol-2-yl group, a 5,8-dimethoxy-1,2,3,4-tetrahydroisoquinol-2-yl group, a 1,2,3,4-tetrahydro-9H-pyrido[3,4-b]indol-2-yl group, a 1,2,3,4-tetrahydro-9H-pyrido[4,3-b]indol-3-yl group, a 4,5,6,7-tetrahydrothieno[2,3-c]pyrid-6-yl group, a 2,3-dihydro-1H-isoindol-2-yl group or a 2,3,4,5-tetra-hydro-1H-3-benzazepin-3-yl group, the respective formulae of which are as follows:

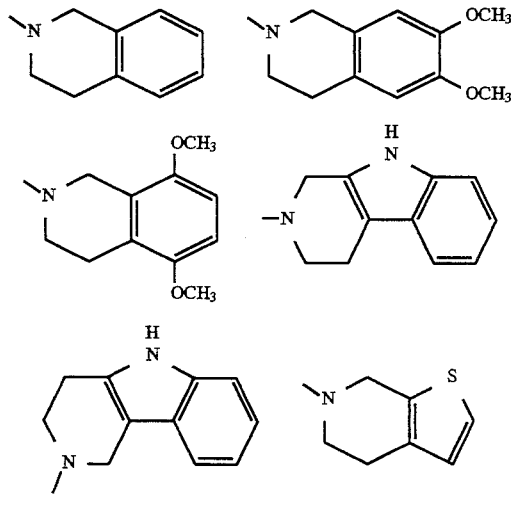

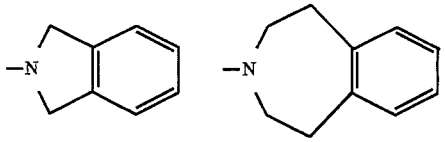

provided that, when $R_1$ is alkoxy and each of $R'_1$ and $R''_1$ is hydrogen, $R_3$ and $R_4$ do not form, with the nitrogen atom, an unsubstituted or substituted tetrahydroisoquinol-2-yl group.

Preferred compounds of the invention, are those in whose formula $R_1$ represents a halogen atom, $R'_1$ represents a hydrogen or halogen atom, $R''_1$ represents a hydrogen atom, $R_3$, taken alone, represents a $C_1$–$C_3$ alkyl group, $R_4$, taken alone, represents a 2,3-dihydro-1H-inden-2-yl group, a 2,3-dihydro-1H-inden-1-yl group or a 1,2,3,4-tetrahydronaphthalen-1-yl group, or alternatively $R_3$ and $R_4$ together form, with the nitrogen atom to which they are attached, a 1,2,3,4-tetrahydroisoquinol-2-yl group, a 6,7-dimethoxy-1,2,3,4-tetrahydroisoquinol-2-yl group or a 5,8-dimethoxy-1,2,3,4-tetrahydroisoquinol-2-yl group.

Among these preferred compounds, the most advantageous are N-[3-[(2,3-dihydro-1H-inden-2-yl)methylamino]propyl]-N-(3,4-dichlorophenyl)-5,6,7,8-tetrahydronaphthalene-2-carboxamide, N-[3-[(2,3-dihydro-1H-inden-1-yl)methylamino]propyl]-N-(3,4,-dichlorophenyl)-5,6,7,8-tetrahydronaphthalene-2-carboxamide, and N-[3-[(1,2,3,4-tetrahydronaphthalen-1-yl)methylamino]propyl]-N-(3,4-dichlorophenyl)-5,6,7,8-tetrahydronaphthalene-2-carboxamide.

The compounds of the invention may exist in the form of bases or acid addition salts.

Moreover, when $R_4$ contains an asymmetric carbon atom, that is to say when $R_4$ represents a 2,3-dihydro-1H-inden-1-yl group or a 1,2,3,4-tetrahydronaphthalen-1-yl group, the compounds may exist in the form of pure optical isomers or mixtures of such isomers.

According to a feature of the invention, the compounds of formula (I) are prepared according to a process illustrated by the following reaction scheme:

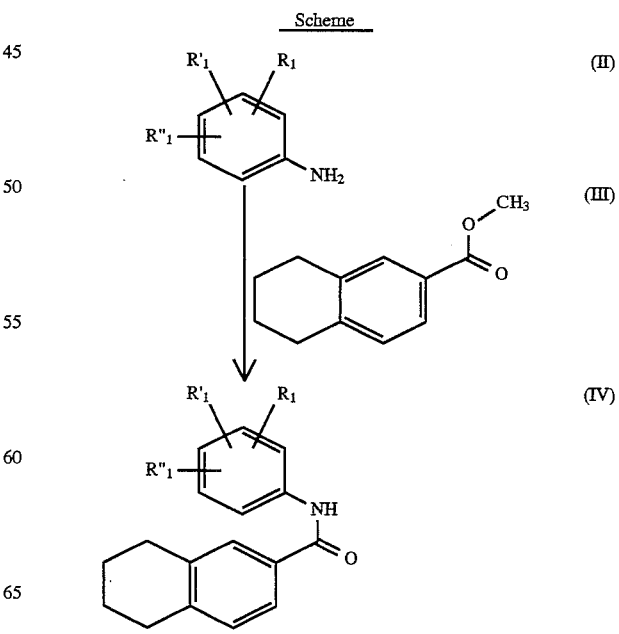

-continued
Scheme

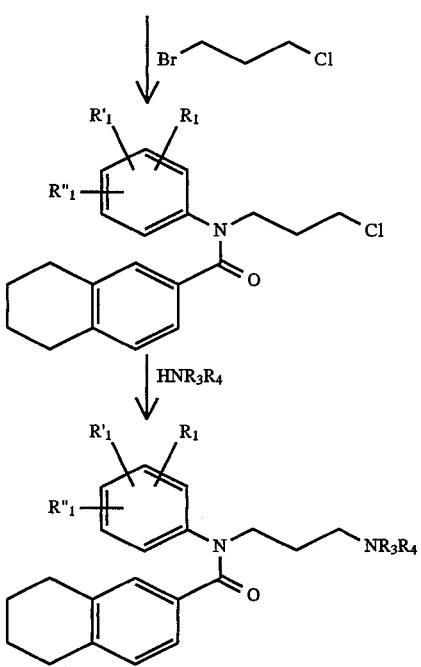

A benzenamine of general formula (II), in which $R_1$, $R'_1$ and $R''_1$ are as defined above, is reacted with methyl 5,6,7,8-tetrahydronaphthalene-2-carboxylate of formula (III), for example in the presence of sodium hydride and in a solvent such as dimethyl sulphoxide. An amide of general formula (IV) is obtained, which is then reacted with 1-bromo-3-chloro-propane of formula (V), for example in the presence of sodium hydride and in a solvent such as N,N-dimethyl-formamide.

A chloro derivative of general formula (VI) is obtained, which is finally reacted with an amine of general formula $HNR_3R_4$, in which $R_3$ and $R_4$ are as defined above, for example in the presence of potassium iodide and of a base such as potassium carbonate, in a solvent such as N,N-dimethylformamide.

The benzenamines of general formula (II) are commercially available, are described in the literature, for example in European Patent Applications EP-A-0,144,730 and EP-A-0,300,865, or are available by methods described in the literature or known to those skilled in the art.

Methyl 5,6,7,8-tetrahydronaphthalene-2-carboxylate is described in J. Amer. Chem. Soc. (1943) 65 1097.

The amines of general formula (VII), in which $R_4$ represents a 2,3-dihydro-1H-inden-2-yl group, are described in J. Med. Chem. (1980) 23 745.

The amines of general formula (VII), in which $R_4$ represents a 2,3-dihydro-1H-inden-1-yl group, are described in J. Amer. Chem. Soc. (1966) 88 2233.

The amines of general formula (VII), in which $R_4$ represents a 1,2,3,4-tetrahydronaphthalen-1-yl group, are described in J. Amer. Chem. Soc. (1960) 82 459, in C. R. Hebd. Seances Acad. Sci. Ser. C. (1969) 268 2225 and in J. Med. Chem. (1966) 9 830.

The 1,2,3,4-tetrahydroisoquinol-2-yl derivatives corresponding to the general formula (VII) are commercially available or are described in the literature.

The 1,2,3,4-tetrahydro-9H-pyrido[3,4-b]indole corresponding to the general formula (VII) is described in Organic Synthesis (1971) 56 136.

The 1,2,3,4-tetrahydro-9H-pyrido[4,3-b]indole corresponding to the general formula (VII) is described in J. Chem. Soc. (1968) 1235.

The 4,5,6,7-tetrahydrothieno[2,3-c]pyridine corresponding to the general formula (VII) is described in Arkiv. Kemi (1970) 13(19) 217.

The 2,3,-dihydro-1H-isoindole corresponding to the general formula (VII) is described in Organic Synthesis Coll. (1973) 5 406.

The 2,3,4,5-tetrahydro-1H-3-benzazepine corresponding to the general formula (VII) is described in Helv. Chim. Acta (1935) 18 1388.

The Examples which follow illustrate in detail the preparation of compounds according to the invention. The elemental microanalyses and the I.R. and N.M.R. spectra confirm the structures of the compounds obtained. The numbers indicated in parentheses in the example titles correspond to those in the 1st column of the Table given later.

EXAMPLE 1

(Compound No. 2)

N-[3-[(2,3-dihydro-1H-inden-2-yl)methylamino]propyl]-N-(3,4-dichlorophenyl)-5,6,7,8-tetrahydronaphthalene-2-carboxamide ethanedioate (1:1) and (E)-2-butenedioate (1:1)

1.1. N-(3,4-Dichlorophenyl)-5,6,7,8-tetrahydronaphthalene-2-carboxamide.

To a suspension of 1.008 g (0.021 mol) of sodium hydride (50% in oil) in 8 ml of dimethyl sulphoxide, under an argon atmosphere, is added one drop of methanol. The mixture is left to stir for 10 min., and 1.94 g (0.012 mol) of 3,4-dichloro-benzenamine are added. The mixture is stirred for 15 min, 2.0 g (0.0105 mol) of methyl 5,6,7,8-tetrahydronaphthalene-2-carboxylate dissolved in 8 ml of dimethyl sulphoxide are added dropwise, and the stirring is continued at room temperature for 3 h. 150 ml of water, 50 ml of diethyl ether, and 50 ml of ethyl acetate are added slowly, and the organic phase is separated, washed successively with 50 ml of water and 50 ml of saturated aqueous sodium chloride solution, dried over magnesium sulphate and filtered. The solvent is evaporated. The residue is crystallized from a mixture of diethyl ether and hexane, and 2.09 g of product are obtained, which is used as it is in the following step.

1.2. N-(3-Chloropropyl)-N-(3,4-dichlorophenyl)-5,6,7,8-tetrahydronaphthalene-2-carboxamide.

To a solution of 2.05 g (0.0064 mol) of N-(3,4-dichlorophenyl)-5,6,7,8-tetrahydronaphthalene-2-carboxamide in 11 ml of N,N-dimethylformamide, under a nitrogen atmosphere, is added slowly, in small portions, 0.369 g (0.0077 mol) of sodium hydride as a 50% suspension in oil. The mixture is cooled to 0° C. 1.26 g (0.008 mol) of 1-bromo-3-chloropropane are added dropwise. The mixture is allowed to return to room temperature and stirring is continued for 4 h.

The mixture is cooled, 50 ml of water and 50 ml of diethyl ether are added slowly, the phases are separated and the aqueous phase is extracted with 50 ml of diethyl ether. The organic phases are combined and are washed successively with twice 50 ml of water, with 50 ml of 1N hydrochloric acid, with twice 50 ml of water and with 50 ml of saturated aqueous sodium chloride solution, dried over magnesium sulphate and the solvent is evaporated. 2.51 g of product are obtained, which is used as it is in the following step.

1.3. N-[3-[(2,3-Dihydro-1H-inden-2-yl)methylamino]propyl]-N-(3,4-dichlorophenyl) -5,6,7,8-tetrahydronaphthalene-2-carboxamide ethanedioate (1:1).

To a solution of 2.45 g (0.0062 mol) of N-(3-chloropropyl)-N-(3,4-dichlorophenyl)-5,6,7,8-tetrahydronaphthalene-2-carboxamide in 9 ml of N,N-dimethylformamide, under an argon atmosphere, are added 1.71 g (0.0124 mol) of potassium carbonate and 1.03 g (0.0062 mol) of potassium iodide followed, after 5 min, by 1.14 g (0.0062 mol) of N-methyl-2,3-dihydro-1H-inden2-amine hydrochloride and the mixture is heated at 85° C. for 4 h.

The mixture is allowed to cool, 50 ml of water and 50 ml of diethyl ether are added, the phases are separated and the aqueous phase is extracted with twice 50 ml of diethyl ether. The organic phases are combined and washed with 50 ml of saturated aqueous sodium chloride solution and dried over magnesium sulphate, and the solvent is evaporated. 3.04 g of oily product are obtained, which is purified by chromatography on a column of silica gel, eluting with a 97/3 dichloromethane/methanol mixture. 0.930 g of pure base is obtained in the form of an oil.

The oxalate is prepared in 2-propanol by adding 0.165 g (0.0018 mol) of oxalic acid to 0.930 g (0.0018 mol) of base, and the product is isolated and recrystallized from ethyl acetate. 0.64 g of oxalate is finally obtained in the form of white crystals.

Melting point: 140°–141° C.

1.4. N-[3-[(2,3-Dihydro-1H-inden-2-yl)methylamino]propyl]-N-(3,4-dichlorophenyl) -5,6,7,8tetrahydronaphthalene-2-carboxamide (E)-2-butenedioate (1:1).

The fumarate is prepared in a mixture of 2-propanol and diisopropyl ether, by adding 1.05 g (0.009 mol) of fumaric acid to 4.58 g (0.009 mol) of base. The salt is isolated and recrystallized from a mixture of 2-propanol and diisopropyl ether. 4.28 g of fumarate are finally obtained in the form of white crystals. Melting point: 160°–116° C.

EXAMPLE 2

(Compound No. 13)

N-(4-Chlorophenyl)-N-[3-(6,7-dimethoxy-1,2,3,4-tetrahydroisoquinol-2-yl)propyl]-5,6,7,8-tetrahydronaphthalene-2-carboxamide ethanedioate 2.1. N-(4-Chlorophenyl)-5,6,7,8-tetrahydronaphthalene-2-carboxamide.

To a suspension of 0.912 g (0.019 mol) of sodium hydride (50% in oil) in 7 ml of dimethyl sulphoxide, under an argon atmosphere, is added one drop of methanol. The mixture is left to stir for 10 min, and 1.40 g (0.011 mol) of 4-chlorobenzenamine are added. The mixture is stirred for 15 min, 1.8 g (0.0095 mol) of methyl 5,6,7,8-tetrahydronaphthalene-2-carboxylate dissolved in 7 ml of dimethyl sulphoxide are added dropwise and the stirring is continued at room temperature for 3 h. 150 ml of water, 50 ml of diethyl ether and 50 ml of ethyl acetate are added slowly, and the organic phase is separated out, washed successively with 50 ml of water and 50 ml of saturated aqueous sodium chloride solution, dried over magnesium sulphate and filtered. The solvent is evaporated. The residue is crystallized from diethyl ether and 1.96 g of product are obtained, which is used as it is in the following step.

2.2. N-(4-Chlorophenyl)-N-(3-chloropropyl)-5,6,7,8-tetrahydronaphthalene-2-carboxamide.

To a solution of 1.92 g (0.0067 mol) of N-(4-chlorophenyl)-5,6,7,8-tetrahydronaphthalene-2-carboxamide in 11 ml of N,N-dimethylformamide, under a nitrogen atmosphere, is added slowly, in small portions, 0.384 g (0.0080 mol) of sodium hydride as a 50% suspension in oil. The mixture is cooled to 0° C. 1.325 g (0.0084 mol) of 1-bromo-3-chloropropane are added dropwise. The mixture is allowed to return to room temperature and stirring is continued for 4 h.

The mixture is cooled, and 50 ml of water and 50 ml of diethyl ether are added slowly. The phases are separated and the aqueous phase is extracted with 50 ml of diethyl ether. The organic phases are combined and are washed successively with twice 50 ml of water, with 50 ml of 1N hydrochloric acid, with twice 50 ml of water and with 50 ml of saturated aqueous sodium chloride solution and dried over magnesium sulphate, and the solvent is evaporated. 2.29 g of product are obtained, which product is used as it is in the following step.

2.3. N-(4-Chlorophenyl)-N-[3-(6,7-dimethoxy-1,2,3,4-tetrahydroisoquinol-2-yl)propyl]-5,6,7,8-tetrahydronaphthalene-2-carboxamide ethanedioate.

To a solution of 2.29 g (0.0063 mol) of N-(4-chlorophenyl)-N-(3-chloropropyl)-5,6,7,8-tetrahydronaphthalene-2-carboxamide in 9 ml of N,N-dimethylformamide, under an argon atmosphere, are added 1.738 g (0.0126 mol) of potassium carbonate and 1.04 g (0.0063 mol) of potassium iodide followed, after 5 min, by 1.45 g (0.0063 mol) of 6,7-dimethoxy-1,2,3,4-tetrahydroisoquinoline hydrochloride and the mixture is heated at 85° C. for 4 h.

The mixture is allowed to cool, 50 ml of water and 50 ml of diethyl ether are added, the phases are separated and the aqueous phase is extracted with twice 50 ml of diethyl ether. The organic phases are combined and washed with 50 ml of saturated aqueous sodium chloride solution and dried over magnesium sulphate. The solvent is evaporated. 3.1 g of oily product are obtained, which is purified by chromatography on a column of silica gel, eluting with a 97/3 dichloromethane/methanol mixture. 1.33 g of pure base are obtained in the form of an oil.

The oxalate is prepared in 2-propanol by adding 0.230 g (0.0025 mol) of oxalic acid to 1.32 g (0.0025 mol) of base, and the product is isolated and recrystallized from 2-propanol. 1.0 g of oxalate is finally obtained in the form of white crystals.

Melting point: 162°–163° C.

EXAMPLE 3

(Compound No. 17)

N-[3-(6,7-Dimethoxy-1,2,3,4-tetrahydroisoquinol-2-yl)propyl]-N-(4-methylphenyl)-5,6,7,8-tetrahydronaphthalene-2-carboxamide ethanedioate 3.1. N-(4-Methylphenyl)-5,6,7,8-tetrahydronaphthalene-2-carboxamide.

To a suspension of 0.912 g (0.019 mol) of sodium hydride (at a content of 50% in oil) in 7 ml of dimethyl sulphoxide, under an argon atmosphere, is added one drop of methanol. The mixture is left to stir for 10 min, and 1.177 g (0.011 mol) of 4-methylbenzenamine are added. The mixture is stirred for 15 min, 1.8 g (0.0095 mol ) of methyl 5,6,7,8-tetrahydronaphthalene-2-carboxylate dissolved in 7 ml of dimethyl sulphoxide are added dropwise, and the stirring is continued at room temperature for 3 h. 150 ml of water, 50 ml of diethyl ether and 50 ml of ethyl acetate are added slowly, and the organic phase is separated, washed successively with 50 ml of water and 50 ml of saturated aqueous sodium chloride solution, dried over magnesium sulphate and filtered. The solvent is evaporated. The residue is crystallized from diethyl ether and 1.43 g of product are obtained, which is used as it is in the following step.

3.2. N-(3-Chloropropyl)-N-(4-methylphenyl)-5,6,7,8-tetrahydronaphthalene-2-carboxamide.

To a solution of 1.4 g (0.0053 mol) of N-(4-methylphenyl)-5,6,7,8-tetrahydronaphthalene-2-carboxamide in 9 ml of N,N-dimethylformamide, under a nitrogen atmosphere, is added slowly, in small portions, 0.307 g (0.0064 mol) of sodium hydride as a 50%. suspension in oil. The mixture is cooled to 0° C., 1.048 g (0.0066 mol) of 1-bromo-3-chloropropane are added dropwise. The mixture is allowed to return to room temperature and stirring is continued for 4 h.

The mixture is cooled, 50 ml of water and 50 ml of diethyl ether are added slowly, the phases are separated and the aqueous phase is extracted with 50 ml of diethyl ether. The organic phases are combined and are washed successively with twice 50 ml of water, with 50 ml of 1N hydrochloric acid, with twice 50 ml of water and with 50 ml of saturated aqueous sodium chloride solution and dried over magnesium sulphate, and the solvent is evaporated. 1.55 g of product are obtained, which is used as it is in the following step.

3.3. N-[3-(6,7-Dimethoxy-1,2,3,4-tetrahydroisoquinol-2-yl) propyl]-N-(4-methylphenyl)-5,6,7,8-tetrahydronaphthalene-2-carboxamide ethanedioate.

To a solution of 1.55 g (0.0045 mol) of N-(3-chloropropyl)-N-(4-methylphenyl)-5,6,7,8-tetrahydronaphthalene-2-carboxamide in 7 ml of N,N-dimethylformamide, under an argon atmosphere, are added 1.24 g (0.009 mol) of potassium carbonate and 0.747 g (0.0045 mol) of potassium iodide followed, after 5 min, by 1.03 g (0.0045 mol) of 6,7-dimethoxy-1,2,3,4-tetrahydroisoquinoline hydrochloride and the mixture is heated at 85° C. for 4 h.

The mixture is allowed to cool, 50 ml of water and 50 ml of diethyl ether are added, the phases are separated and the aqueous phase is extracted with twice 50 ml of diethyl ether. The organic phases are combined and washed with 50 ml of saturated aqueous sodium chloride solution and dried over magnesium sulphate. The solvent is evaporated. 2.07 g of oily are obtained, which product is purified by chromatography on a column of silica gel, eluting with a 97/3 dichloromethane/methanol mixture. 0.920 g of pure base is obtained in the form of an oil.

The oxalate is prepared in 2-propanol by adding 0.162 g (0.0018 mol) of oxalic acid to 0.9 g (0.0018 mol) of base, and the product is isolated and recrystallized from 2-propanol. 0.797 g of oxalate is finally obtained in the form of white crystals.

Melting point: 159°–160° C.

EXAMPLE 4

(Compound No. 26)

N-[4-(2-Methylpropoxy)phenyl]-N-[3-(1,2,3,4-tetrahydro-9H-pyrido[4,3-b]indol-3-yl)propyl]-5,6,7,8-tetrahydronaphthalene-2-carboxamide ethanedioate 4.1. N-[4-(2-Methylpropoxy)phenyl]acetamide.

To a solution of 23 g (0.15 mol) of N-(4-hydroxyphenyl) acetamide in 124 ml of N,N-dimethylformamide are added 32.6 ml (0.3 mol ) of 1-bromo-2-methylpropane and 31 g (0.225 mol) of potassium carbonate, and the mixture is heated at 100° C. for 5 h. The mixture is cooled, the solvent is evaporated, and the residue is taken up in 400 ml of diethyl ether and 200 ml of 1N sodium hydroxide. The organic phase is separated and washed successively with three times 50 ml of 1N sodium hydroxide, with three times 100 ml of water and with 50 ml of saturated aqueous sodium chloride solution, dried over magnesium sulphate and filtered. The solvent is evaporated. 30.96 g of product are obtained, which is used as it is in the following step.

4.2. 4-(2-Methylpropoxy)benzenamine.

To a solution of 30.35 g (0.146 mol) of N-[4-(2-methylpropoxy)phenyl]acetamide in 157 ml of ethanol are added 41.5 ml (0.309 mol) of 30% sodium hydroxide, and the mixture is heated to reflux for 5 h. The solvent is evaporated and the residue is taken up in 400 ml of diethyl ether and 350 ml of water. The organic phase is separated and washed successively with three times 100 ml of water and with 50 ml of saturated aqueous sodium chloride solution, dried over magnesium sulphate and filtered. The solvent is evaporated. 23.64 g of product are obtained, which is purified by chromatography on a column of silica gel, eluting with a 7/3 cyclohexane/ethyl acetate mixture. 22.43 g of product are obtained.

4.3. N-[4-(2-Methylpropoxy)phenyl]-5,6,7,8-tetrahydronaphthalene-2-carboxamide.

To a suspension of 1.25 g (0.026 mol) of sodium hydride (at a content of 50% in oil) in 10 ml of dimethyl sulphoxide, under an argon atmosphere, is added one drop of methanol, the mixture is left stirring for 10 min and 2.6 g (0.015 mol) of 4-(2-methylpropoxy)benzenamine are added. The mixture is stirred for 15 min, 2.5 g (0.013 mol) of methyl 5,6,7,8-tetrahydronaphthalene-2-carboxylate dissolved in 10 ml of dimethyl sulphoxide are added dropwise and the stirring is continued at room temperature for 3 h. 200 ml of water, 100 ml of diethyl ether and 100 ml of ethyl acetate are added slowly, the organic phase is separated and is washed successively with 100 ml of water, with 100 ml of 1N hydrochloric acid, with twice 50 ml of water and with 100 ml of saturated aqueous sodium chloride solution, dried over magnesium sulphate and filtered. The solvent is evaporated.

The residue is crystallized from a mixture of diethyl ether and hexane, and 3.10 g of product are obtained, which is used as it is in the following step.

4.4. N-(3-Chloropropyl)-N-[4-(2-methylpropoxy)phenyl]-5,6,7,8-tetrahydronaphthalene-2-carboxamide.

To a solution of 2.5 g (0.008 mol) of N-[4-(2-methylpropoxy)phenyl]-5,6,7,8-tetrahydronaphthalene-2-carboxamide in 13 ml of N,N-dimethylformamide, under a nitrogen atmosphere, is added slowly, in small portions, 0.5 g (0.010 mol) of sodium hydride as a 50% suspension in oil. The mixture is cooled to 0° C. 1.6 g (0.010 mol ) of 1-bromo-3-chloropropane are added dropwise, the mixture is allowed to return to room temperature and stirring is continued for 4 h. The mixture is cooled. 100 ml of water and 100 ml of diethyl ether are added slowly. The phases are separated and the aqueous phase is extracted with 100 ml of diethyl ether. The organic phases are combined and are washed successively with twice 50 ml of water, with 50 ml of 1N hydrochloric acid, with twice 50 ml of water and with 50 ml of saturated aqueous sodium chloride solution, and dried over magnesium sulphate. The solvent is evaporated. 3.13 g of product are obtained, which is used as it is in the following step.

4.5. N-[4-(2-Methylpropoxy)phenyl]-N-[3-(1,2,3,4-tetrahydro-9H-pyrido[4,3-b]indol-3-yl)-propyl]-5,6,7,8-tetrahydronaphthalene-2-carboxamide ethanedioate.

To a solution of 3.13 g (0.008 mol) of N-(3-chloropropyl)-N-[4-(2-methylpropoxy)phenyl]-5,6,7,8-tetrahydronaphthalene-2-carboxamide in 11 ml of N,N-dimethylformamide, under an argon atmosphere, are added 2.21 g (0.016 mol) of potassium carbonate and 1.33 g (0.008 mol) of potassium iodide followed, after 5 min, by 1.67 g (0.008 mol) of 1,2,3,4-tetrahydro-9H-pyrido[4,3-b]indole hydrochloride and the mixture is heated at 85° C. for 4 h. The mixture is allowed to cool, 100 ml of water and 100 ml of diethyl ether are added, the phases are separated and the aqueous phase is extracted with twice 50 ml of diethyl ether. The organic phases are combined and washed with 100 ml of saturated aqueous sodium chloride solution and dried over magnesium sulphate, and the solvent is evaporated. 4.29 g of oily product are obtained, which is purified by chromatography on a column of silica gel, eluting with a 95/5 dichloromethane/methanol mixture. 1.63 g of pure base are obtained in the form of an oil.

The oxalate is prepared in 2-propanol by adding 0.221 g (0.0025 mol) of oxalic acid to 1.32 g (0.0025 mol) of base, and the product is isolated and recrystallized from 2-propanol. 1.0 g of oxalate is finally isolated in the form of white crystals.

Melting point: 121°–122° C.

EXAMPLE 5

(Compound No. 20)

N-(4-Methoxyphenyl)-N-[3-(1,2,3,4-tetrahydro-9H-pyrido[3,4-b]indol-2-yl)propyl]-5,6,7,-tetarahydronaphthalene-2-carboxamide ethanedioate 5.1. N-(4-Methoxyphenyl)-5,6,7,8-tetrahydronaphthalene-2-carboxamide.

To a suspension of 1.25 g (0.026 mol) of sodium hydride (at a content of 50% in oil) in 10 ml of dimethyl sulphoxide, under an argon atmosphere, is added one drop of methanol, the mixture is left to stir for 10 min, and 1.92 g (0.015 mol) of 4-methoxybenzenamine are added. The mixture is left to stir for 15 min, 2.5 g (0.013 mol) of methyl 5,6,7,8-tetrahydronaphthalene-2-carboxylate dissolved in 10 ml of dimethyl sulphoxide are added dropwise and the stirring is continued at room temperature for 3 h. 200 ml of water, 100 ml of diethyl ether and 100 ml of ethyl acetate are added slowly, and the organic phase is separated and is washed successively with 100 ml of water, with 100 ml of 1N hydrochloric acid, with twice 50 ml of water and with 100 ml of saturated aqueous sodium chloride solution, dried over magnesium sulphate and filtered, and the solvent is evaporated. 3.34 g of residue are obtained, which is crystallized from a mixture of diethyl ether and hexane. 2.69 g of product are obtained, which is used as it is in the following step.

5.2. N-(3-Chloropropyl)-N-(4-methoxyphenyl)-5,6,7,8-tetrahydronaphthalene-2-carboxamide.

To a solution of 2.47 g (0.0088 mol) of N-(4-methoxyphenyl)-5,6,7,8-tetrahydronaphthalene-2-carboxamide in 14 ml of N,N-dimethylformamide, under a nitrogen atmosphere, is added slowly, in small portions, 0.506 g (0.0105 mol) of sodium hydride as a 50% suspension in oil. The mixture is cooled to 0° C., 1.73 g (0.011 mol) of 1-bromo-3-chloropropane are added dropwise. The mixture is allowed to return to room temperature and stirring is continued for 4 h. The mixture is cooled, 100 ml of water and 100 ml of diethyl ether are added slowly, the phases are separated and the aqueous phase is extracted with 100 ml of diethyl ether. The organic phases are combined and are washed successively with twice 50 ml of water, with 50 ml of 1N hydrochloric acid, with twice 50 ml of water and with 50 ml of saturated aqueous sodium chloride solution, dried over magnesium sulphate and the solvent is evaporated. 3.11 g of product are obtained, which is used as it is in the following step.

5.3. N-(4-Methoxyphenyl)-N-[3-(1,2,3,4-tetrahydro-9H-pyrido[3,4-b]indol-2-yl)propyl]-5,6,7,8-tetrahydronaphthalene-2-carboxamide ethanedioate.

To a solution of 2.28 g (0.0064 mol) of N-(3-chloropropyl)-N-(4-methoxyphenyl)-5,6,7,8-tetrahydronaphthalene-2-carboxamide in 8 ml of N,N-dimethylformamide, under an argon atmosphere, are added 1.76 g (0.0128 mol) of potassium carbonate and 1.06 g (0.0064 mol) of potassium iodide followed, after 5 min, by 1.1 g (0.0064 mol) of 1,2,3,4-tetrahydro-9H-pyrido[3,4-b] indole hydrochloride and the mixture is heated at 85° C. for 4 h. The mixture is allowed to cool. 100 ml of water and 100 ml of diethyl ether are added. The phases are separated and the aqueous phase is extracted with twice 50 ml of diethyl ether. The organic phases are combined and washed with 100 ml of saturated aqueous sodium chloride solution and dried over magnesium sulphate, and the solvent is evaporated. 2.66 g of oily product are obtained, which is purified by chromatography on a column of silica gel, eluting with a 97/3 dichloromethane/methanol mixture. 0.930 g of pure base is obtained in the form of an oil.

The oxalate is prepared in 2-propanol by adding 0.170 g (0.0019 mol) of oxalic acid to 0.930 g (0.0019 mol) of base, and the product is isolated and recrystallized from 2-propanol. 0.515 g of oxalate is finally obtained in the form of white crystals.

Melting point: 245° C.

EXAMPLE 6

(Compound No. 28)

N-(4-Chlorophenyl)-N-[3-(2,3,4,5-tetrahydro-1H-3-benzazepin-3-yl)propyl]-5,6,7,8-tetrahydronaphthalene-2-carboxamide ethanedioate 6.1. N-(4-Chlorophenyl)-5,6,7,8-tetrahydronaphthalene-2-carboxamide.

To a suspension of 0.912 g (0.019 mol) of sodium hydride (at a content of 50% in oil) in 7 ml of dimethyl sulphoxide, under an argon atmosphere, is added one drop of methanol. The mixture is left to stir for 10 min, and 1.40 g (0.011 mol) of 4-chlorobenzenamine are added. The mixture is left to stir for 15 min, 1.8 g (0.0095 mol) of methyl 5,6,7,8-tetrahydronaphthalene-2-carboxylate dissolved in 7 ml of dimethyl sulphoxide are added dropwise and the stirring is continued at room temperature for 3 h. 150 ml of water, 50 ml of diethyl ether and 50 ml of ethyl acetate are added slowly, and the organic phase is separated and washed successively with 50 ml of water and 50 ml of saturated aqueous sodium chloride solution, dried over magnesium sulphate and filtered. The solvent is evaporated. 2.5 g of residue are obtained, which is crystallized from diethyl ether. 1.96 g of product are obtained, which product is used as it is in the following step.

6.2. N-(4-Chlorophenyl)-N-(3-chloropropyl)-5,6,7,8-tetrahydronaphthalene-2-carboxamide.

To a solution of 1.92 g (0.0067 mol) of N-(4-chlorophenyl)-5,6,7,8-tetrahydronaphthalene-2-carboxamide in 11 ml of N,N-dimethylformamide, under a nitrogen atmosphere, is added slowly, in small portions, 0.384 g (0.008 mol) of sodium hydride as a 50% suspension in oil. The mixture is cooled to 0° C. 1.325 g (0.0084 mol) of 1-bromo-3-chloropropane are added dropwise. The mixture is allowed to return to room temperature and stirring is continued for 4 h. The mixture is cooled, 50 ml of water and 50 ml of diethyl ether are added slowly, the phases are separated and the aqueous phase is extracted with 50 ml of diethyl ether. The organic phases are combined and washed successively with twice 50 ml of water, with 50 ml of 1N hydrochloric acid, with twice 50 ml of water and with 50 ml of saturated aqueous sodium chloride solution, and dried over magnesium sulphate. The solvent is evaporated. 2.29 g of product are obtained, which is used as it is in the following step.

6.3. N-(4-Chlorophenyl)-N-[3-(2,3,4,5-tetrahydro-1H-3-benzazepin-3-yl)propyl]-5,6,7,8-tetrahydronaphthalene-2-carboxamide ethanedioate.

To a solution of 2.5 g (0.0069 mol) of N-(4-chlorophenyl)-N-(3-chloropropyl)-5,6,7,8-tetrahydronaphthalene-2-carboxamide in 9 ml of N,N-dimethylformamide, under an argon atmosphere, are added 1.9 g (0.0138 mol ) of potassium carbonate and 1.14 g (0.0069 mol ) of potassium iodide followed, after 5 min, by 1.26 g (0.0069 mol) of 2,3,4,5-tetrahydro-1H-3-benzazepine hydrochloride and the mixture is heated at 85° C. for 4 h. The mixture is allowed to cool. 50 ml of water and 50 ml of diethyl ether are added. The phases are separated and the aqueous phase is extracted with twice 50 ml of diethyl ether. The organic phases are combined and washed with 50 ml of saturated aqueous sodium chloride solution and dried over magnesium sulphate. The solvent is evaporated. 3.04 g of oily product are obtained, which is purified by chromatography on a column of silica gel, eluting with a 97/3 dichloromethane/methanol mixture. 1.18 g of pure base are obtained in the form of an oil.

The oxalate is prepared in 2-propanol by adding 0.225 g (0.0025 mol) of oxalic acid to 1.18 g (0.0025 mol) of base, and the product is isolated and recrystallized from 2-propanol. 1.04 g of oxalate are finally obtained in the form of white crystals.

Melting point: 180° C.

EXAMPLE 7

(Compound No. 27)

N-(4-Chlorophenyl)-N-[3-(4,5,6,7-tetrahydrothieno-[2,3-c]pyrid-6-yl)propyl]-5,6,7,8-tetrahydronaphthalene-2-carboxamide ethanedioate (1:1)

To a solution of 2.37 g (0.0065 mol) of N-(4-chlorophenyl)-N-(3-chloropropyl)-5,6,7,8-tetrahydronaphthalene-2-carboxamide in 10 ml of N,N-dimethylformamide, under an argon atmosphere, are added 2.69 g (0.0195 mol) of potassium carbonate and 1.1 g (0.0065 mol) of potassium iodide followed, after 5 min, by 1.49 g (0.0065 mol) of 4,5,6,7-tetrahydrothieno[2,3-c]pyridine oxalate and the mixture is heated at 85° C. for 4 h. The mixture is allowed to cool. 50 ml of water and 50 ml of diethyl ether are added. The phases are separated and the aqueous phase is extracted with twice 50 ml of diethyl ether. The organic phases are combined and washed with 50 ml of saturated aqueous sodium chloride solution and dried over magnesium sulphate. The solvent is evaporated. 3.0 g of oily product are obtained, which is purified by chromatography on a column of silica gel, eluting with a 97/3 dichloromethane/methanol mixture. 1.16 g of pure base are obtained in the form of an oil.

The oxalate is prepared in 2-propanol by adding 0.26 g (0.0022 mol) of oxalic acid to 1.16 g (0.0022 mol) of base, and the product is isolated and recrystallized from 2-propanol. 1.09 g of oxalate are finally obtained in the form of white crystals.

Melting point: 164°–165° C.

EXAMPLE 8

(Compound No. 31)

N-(4-Chlorophenyl)-N-[3-(2,3-dihydro-1H-isoindol-2-yl)propyl]-5,6,7,8-tetrahydronaphthalene-2-carboxamide (E)-2-butenedioate (1:1)

To a solution of 2.0 g (0.0055 mol) of N-(4-chlorophenyl)-N-(3-chloropropyl)-5,6,7,8-tetrahydronaphthalene-2-carboxamide in 10 ml of N,N-dimethylformamide, under an argon atmosphere, are added 1.15 g (0.0083 mol) of potassium carbonate and 0.92 g (0.0055 mol) of potassium iodide followed, after 5 min, by 0.66 g (0.0055 mol) of 2,3-dihydro-1H-isoindole. The mixture is heated at 85° C. for 4 h. The mixture is allowed to cool. 50 ml of water and 50 ml of diethyl ether are added. The phases are separated and the aqueous phase is extracted with twice 50 ml of diethyl ether. The organic phases are combined and washed with 50 ml of saturated aqueous sodium chloride solution and dried over magnesium sulphate. The solvent is evaporated. 2.8 g of oily product are obtained, which product is purified by chromatography on a column of silica gel, eluting with a 97/3 dichloromethane/methanol mixture. 0.82 g of pure base is obtained in the form of an oil.

The fumarate is prepared in 2-propanol by adding 0.21 g (0.0018 mol) of fumaric acid to 0.82 g (0.0018 mol) of base, and the product is isolated and recrystallized from 2-propanol. 0.43 g of fumarate is finally obtained in the form of white crystals.

Melting point: 141°–142° C.

EXAMPLE 9

(Compound No. 44)

(±)-N-[3-[(2,3-Dihydro-1H-inden-1-yl)methylamino]-propyl]-N-(3,4-dichlorophenyl)-5,6,7,8-tetrahydronaphthalene-2-carboxamide ethanedioate (1:1)

To a solution of 3 g (0.0075 mol) of N-(3-chloropropyl)-N-(3,4-dichlorophenyl)-5,6,7,8-tetrahydronaphthalene-2-carboxamide in 12 ml of N,N-dimethylformamide, under an argon atmosphere, are added 2.07 g (0.015 mol) of potassium carbonate and 1.25 g (0.0075 mol) of potassium iodide followed, after stirring for 5 min, by 1.37 g (0.0075 mol) of N-methyl-2,3-dihydro-1H-inden-1-amine hydrochloride, and the mixture is heated at 85° C. for 3h 30. The mixture is allowed to cool. 50 ml of water are added and the brown precipitate is separated by filtration, washed with water and dried. 3.58 g of product are obtained, which is purified by chromatography on a column of silica gel, eluting with a 96/4 dichloromethane/methanol mixture. 1.12 g of pure base are obtained.

In order to prepare the oxalate, 0.73 g (0.0014 mol) of base and 0.13 g (0.0014 mol) of oxalic acid are dissolved in 10 ml of 2-propanol. The mixture is heated to reflux until the materials have dissolved, and cooled. The white precipitate is collected and recrystallized from 2-propanol. After filtration and drying, 0.58 g of oxalate is finally obtained.

Melting point: 142°–143° C.

EXAMPLE 10

(Compound No. 45)

(±)-N-[3-[(1,2,3,4-Tetrahydronaphthalen-1-yl) methylamino]propyl]-N-(3,4-dichlorophenyl)-5,6,7, 8-tetrahydronaphthalene-2-carboxamide ethanedioate (1:1)

To a solution of 3 g (0.0075 mol) of N-(3-chloropropyl) -N-(3,4-dichlorophenyl)-5,6,7,8-tetrahydronaphthalene-2-carboxamide in 12 ml of N,N-dimethylformamide, under an argon atmosphere, are added 2.07 g (0.015 mol) of potassium carbonate and 1.25 g (0.0075 mol) of potassium iodide followed, after stirring for 5 min, by 1.48 g (0.0075 mol) of N-methyl-1,2,3,4-tetrahydronaphthalen-1-amine hydrochloride, and the mixture is heated at 85° C. for 3h 30. The mixture is allowed to cool. 50 ml of water are added and the yellow precipitate is separated by filtration, washed with water and dried.

4.32 g of product are obtained, which is purified by chromatography on a column of silica gel, eluting with a 96/4 dichloromethane/methanol mixture. 1.34 g of pure base are obtained in the form of an oil.

In order to prepare the oxalate, the 1.34 g (0.0026 mol) of base and 0.23 g (0.0026 mol) of oxalic acid are dissolved in 15 ml of 2-propanol. The mixture is heated to reflux until the materials have dissolved and the solvent is evaporated. The residue is recrystallized from a large volume of diisopropyl ether and the white precipitate is collected by filtration and dried. 0.71 g of oxalate is finally obtained.

Melting point: 116°–117° C.

The Table which follows illustrates the chemical structures and the physical properties of some compounds according to the invention. In the "Salt" column, "–" denotes a compound in the form of a base, "ox." denotes an oxalate or ethanedioate, "fum." denotes a fumarate or (E)-2-butenedioate, "cit." denotes a citrate or 2-hydroxy-1,2,3-propanetricarboxylate, and "mes." denotes a mesotartrate or 2,3-dihydroxybutanedioate. The ratio indicated in parentheses is the acid:base molar ratio.

TABLE (Structure I shown with substituents $R_1$, $R'_1$, $R''_1$ on phenyl ring; N-CH$_2$CH$_2$CH$_2$-NR$_3$R$_4$; amide-linked tetrahydronaphthalene-2-carbonyl group)

| No. | $R_1$ $R'_1$ $R''_1$ | $R_3$ | $R_4$ | Salt | m.p. (°C.) |
|---|---|---|---|---|---|
| 1 | 4-Cl<br>H<br>H | $CH_3$ | indanyl | fum. (1.5:1) | 132–133 |
| 2 | 3-Cl<br>4-Cl<br>H | $CH_3$ | indanyl | ox. (1:1)<br>fum. (1:1)<br>cit. (1:1)<br>mes. (1:1) | 140–141<br>160–161<br>130–131<br>167–168 |
| 3 | 4-OCH$_2$CH(CH$_3$)$_2$<br>H<br>H | $CH_3$ | indanyl | fum. (1.5:1) | 64–65 |
| 4 | 4-Cl<br>H<br>H | $CH_2CH_2CH_3$ | indanyl | — | 116–117 |
| 5 | 3-Cl<br>4-Cl<br>H | $CH_2CH_2CH_3$ | indanyl | ox. (1.3:1) | 73–74 |
| 6 | 4-OCH$_2$CH(CH$_3$)$_2$<br>H<br>H | $CH_2CH_2CH_3$ | indanyl | fum. (1.5:1) | 64–65 |
| 7 | 2-Cl<br>H<br>H | | tetrahydronaphthyl | ox. (1:1) | 185–186 |

TABLE-continued (I structure: tetrahydronaphthalene-2-carboxamide with N-substituted aryl group bearing R₁, R'₁, R''₁ and N-(CH₂)₃-NR₃R₄)

| No. | R₁ R'₁ R''₁ | R₃ | R₄ | Salt | m.p. (°C.) |
|---|---|---|---|---|---|
| 8 | 2-Cl<br>H<br>H | ethyl | 2-(3,4-dimethoxyphenyl)ethyl | fum. (1:1) | 149–150 |
| 9 | 3-Cl<br>H<br>H | ethyl | 2-phenylethyl | fum. (1:1) | 159–160 |
| 10 | 3-Cl<br>H<br>H | ethyl | 2-(3,4-dimethoxyphenyl)ethyl | fum. (1:1) | 181–182 |
| 11 | 4-Cl<br>H<br>H | ethyl | 2-phenylethyl | fum. (1:1) | 154–155 |
| 12 | 4-Cl<br>H<br>H | ethyl | 2-(2,5-dimethoxyphenyl)ethyl | ox. (1:1.15)<br>fum. (1:1) | 190<br>196–197 |
| 13 | 4-Cl<br>H<br>H | ethyl | 2-(3,4-dimethoxyphenyl)ethyl | ox. (1.15:1) | 162–163 |
| 14 | 4-F<br>H<br>H | ethyl | 2-(3,4-dimethoxyphenyl)ethyl | ox. (1.15:1) | 104–105 |
| 15 | 3-Cl<br>4-Cl<br>H | ethyl | 2-(3,4-dimethoxyphenyl)ethyl | ox. (1.15:1) | 145–146 |
| 16 | 2-OCH₂CH(CH₃)₂<br>5-F<br>H | ethyl | 2-phenylethyl | ox. (1:1) | 190–191 |
| 17 | 4-CH₃<br>H<br>H | ethyl | 2-(3,4-dimethoxyphenyl)ethyl | ox. (1.05:1) | 159–160 |
| 18 | 4-Cl<br>H<br>H | ethyl | 2-(3-indolyl)ethyl | ox. (1.05:1)<br>fum. (1:1) | 229–230<br>205–206 |

TABLE-continued
(I)
| No. | $R_1$ $R'_1$ $R''_1$ | $R_3$ | $R_4$ | Salt | m.p. (°C.) |
|---|---|---|---|---|---|
| 19 | 3-Cl<br>4-Cl<br>H | | 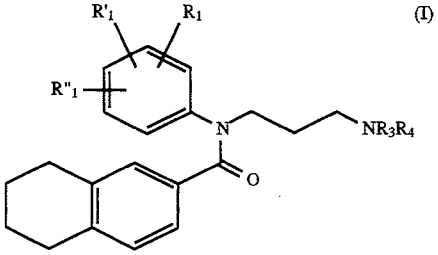 | ox. (1.2:1) | 234–235 |
| 20 | 4-OCH$_3$<br>H<br>H | | 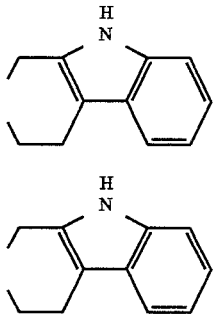 | ox. (1.1:1) | 245 |
| 21 | 2-OCH$_2$CH(CH$_3$)$_2$<br>H<br>H | | 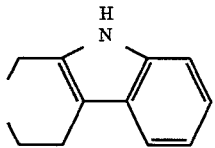 | ox. (1.3:1) | 118–119 |
| 22 | 4-OCH$_2$CH(CH$_3$)$_2$<br>H<br>H | | 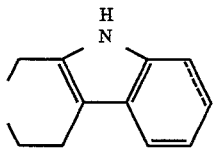 | ox. (1:1) | 117–118 |
| 23 | 4-Cl<br>H<br>H | | 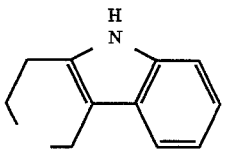 | ox. (1:1) | 144 |
| 24 | 3-Cl<br>4-Cl<br>H | | 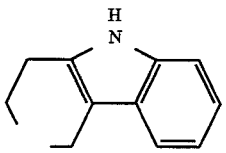 | ox. (1:1) | 134–135 |
| 25 | 4-OCH$_3$<br>H<br>H | | 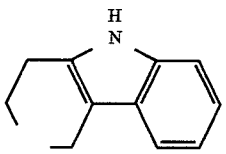 | ox. (1.15:1) | 134–135 |
| 26 | 4-OCH$_2$CH(CH$_3$)$_2$<br>H<br>H | | 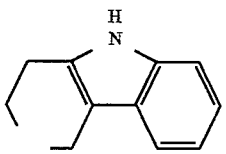 | ox. (1.35:1) | 121–122 |

TABLE-continued
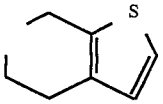
| No. | R₁ R'₁ R"₁ | R₃ | R₄ | Salt | m.p. (°C.) |
|---|---|---|---|---|---|
| 27 | 4-Cl<br>H<br>H | | 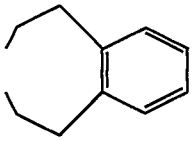 | ox. (1:1) | 164–165 |
| 28 | 4-Cl<br>H<br>H | | 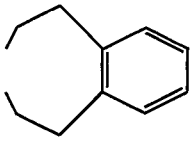 | ox. (1:1) | 180 |
| 29 | 4-OCH₃<br>H<br>H | | 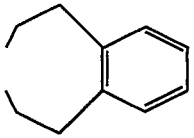 | ox. (1.05:1) | 202–203 |
| 30 | 4-OCH₂CH(CH₃)₂<br>H<br>H | | 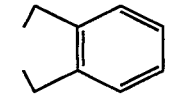 | ox. (1.15:1) | 149–150 |
| 31 | 4-Cl<br>H<br>H | | 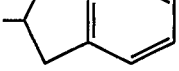 | fum. (1:1) | 141–142 |
| 32 | H<br>H<br>H | CH₃ |  | fum. (1:1) | 159–161 |
| 33 | 2-Cl<br>3-Cl<br>H | CH₃ | 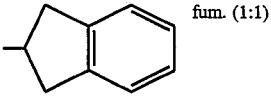 | fum. (1:1) | 119–121 |
| 34 | 3-Cl<br>5-Cl<br>H | CH₃ | 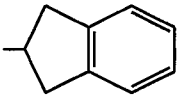 | fum. (1:1) | 177–179 |
| 35 | 2-Cl<br>5-Cl<br>H | CH₃ | | fum. (1:1) | 158–160 |
| 36 | 2-Cl<br>4-Cl<br>H | CH₃ |  | fum. (1:1) | 162–164 |
| 37 | 2-Cl<br>H<br>H | CH₃ | 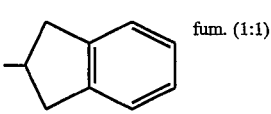 | fum. (1:1) | 169–171 |

TABLE-continued
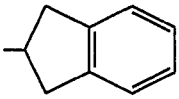
(I)
| No. | $R_1$ $R'_1$ $R''_1$ | $R_3$ | $R_4$ | Salt | m.p. (°C.) |
|---|---|---|---|---|---|
| 38 | 3-Cl<br>H<br>H | $CH_3$ | 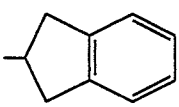 | fum. (1:1) | 157–159 |
| 39 | 4-$CH_3$<br>H<br>H | $CH_3$ | 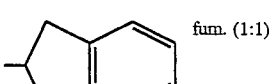 | fum. (1:1) | 153–155 |
| 40 | 4-F<br>H<br>H | $CH_3$ | 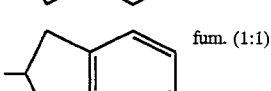 | fum. (1:1) | 157–159 |
| 41 | 4-$OCH_3$<br>H<br>H | $CH_3$ | 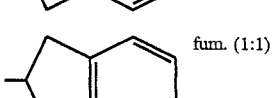 | fum. (1:1) | 146–148 |
| 42 | 2-$OCH_3$<br>H<br>H | $CH_3$ | 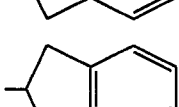 | fum. (1:1) | 155–157 |
| 43 | 3-$OCH_3$<br>H<br>H | $CH_3$ | 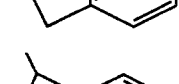 | fum. (1:1) | 159–161 |
| 44 | 3-Cl<br>4-Cl<br>H | $CH_3$ | 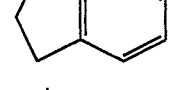 | ox. (1:1) | 142–143 |
| 45 | 3-Cl<br>4-Cl<br>H | $CH_3$ | 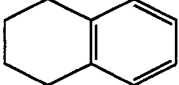 | ox. (1:1) | 116–117 |
| 46 | 2-Cl<br>6-Cl<br>H | $CH_3$ | 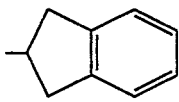 | fum. (1:1) | 201–203 |
| 47 | 2-Cl<br>4-Cl<br>H | $CH_3$ | 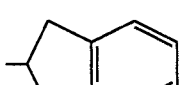 | ox. (1:1) | 141–143 |
| 48 | 3-Cl<br>5-Cl<br>H | $CH_3$ | 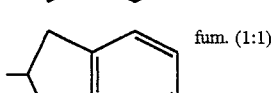 | fum. (1:1) | 87–89 |
| 49 | 2-$CH_3$<br>H<br>H | $CH_3$ |  | fum. (1:1) | 164–166 |

TABLE-continued

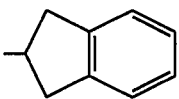

| No. | R₁ R'₁ R"₁ | R₃ | R₄ | Salt | m.p. (°C.) |
|---|---|---|---|---|---|
| 50 | 2-OCH₃<br>3-Cl<br>H | CH₃ | 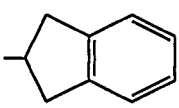 | ox. (1.1:1) | 144–146 |
| 51 | 2-OCH₃<br>5-Cl<br>4-OCH₃ | CH₃ | 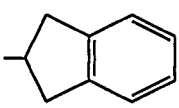 | ox. (1:1) | 118–120 |
| 52 | 3-Cl<br>4-Cl<br>H | | 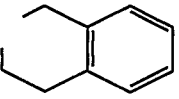 | fum. (1:1) | 158–159 |

The compounds of the invention have been subjected to various tests which have demonstrated their therapeutic utility.

Thus, they were subjected to the global cerebral ischemia test in mice. The ischemia caused by a cardiac arrest induced by rapid intravenous injection of magnesium chloride. In this test, the "survival time" is measured, that is to say the interval between the moment of the injection of magnesium chloride and the final observable respiratory movement of each mouse. This final movement is considered as the ultimate indication of central nervous system functioning. Under the test conditions, respiratory arrest appears approximately 19 seconds after the injection of magnesium chloride.

Male mice (Swiss OF1 IFFA CREDO) are studied in groups of 10. They are given food and drink ad libitum before the tests. The survival time is measured 10 minutes after intraperitoneal administration of the compounds of the invention. The results are given in the form of the difference between the survival time measured in a group of 10 mice which received the compound and the survival time measured in a group of 10 mice which received the vehicle liquid only. The ratios between the changes in the survival time and the dosage of the compound are recorded graphically as a semilogarithmic curve.

This curve makes it possible to calculate the "3 second effective dose" ($ED_3$"), that is to say the dose (in mg/kg) which produces a 3-second increase in the survival time relative to the control group of 10 untreated mice. A 3-second increase in the survival time is both statistically significant and reproducible. The $ED_3$" of the compounds of the invention range from 0.1 to 30 mg/kg when they are administered via the intraperitoneal route.

The compounds of the invention were also the subject of a study of the potential-dependent ("voltage-dependent") barium currents by the so-called "patch-clamp" technique.

The barium currents flowing through the potential-dependent calcium channels are measured on a preparation of new-born rat (Sprague-Dawley) cortex cells in culture (cultured for 6 to 10 days); in the case of these cells, these are composite currents which involve the L, N and P channels, as described in Soc. Neurosci. Abstr. (1989) 15 823.

The measuring chambers, 800 µl in volume, containing the cortex cells, are placed on the stage of an Olympus IMT-2™ inverted microscope and the cells are observed at a magnification of 400×. The chambers are perfused continuously (4 to 5 ml/min) using a solution distributor device having 9 inputs (dead volume <50 µl), the sole outlet of which, consisting of a polyethylene tube with a 500 µm opening, is placed less than 3 mm away from the cell studied. This device has the advantage of allowing a rapid change of solution on the cells studied.

The patch-clamp method used is described in Pfluegers Archives (1981) 391 85–100. An Axopatch-1D™ amplifier connected to an AT 386–33 MHz type computer, using PCLAMP™ software from Axon Instruments™, is used for stimulation of the cells, acquisition of the data and analysis of the results. In order to record the barium currents, borosilicate glass pipettes are brought close to the cells by means of a Narishige WR60™ hydraulic micromanipulator. The tip of the pipettes is filled with the reference intracellular solution, the composition (in mM) of which is as follows: CsCl (140), CaCl₂ (1), Na₂TP (4), EGTA (11; pCa=8), Hepes (10), Tris-OH (pH =7.2).

Once the so-called "whole cell" configuration is obtained, the cell is perfused with a so-called TEA-Barium solution, the composition (in mM) of which is as follows: TEA-Cl (144), BaI₂ (5), MgCl₂ (2), CsCl (3), glucose (10), Hepes (10), Tris-OH (pH =7.4).

This solution makes it possible to measure the calcium current (similar to the barium current flowing through the potential-dependent calcium channels) while at the same time being independent of the sodium and potassium currents.

The global potential-dependent barium current is obtained by application of a depolarizing potential step with a duration of 250 ms, taking the membrane potential from −80 mV to 0 mV. The stimulation frequency is 0.25 Hz.

The compounds of the invention are dissolved in the TEA-barium medium and are applied once the amplitude of the barium current has stabilized. After obtaining a stable inhibitory effect, the cell is again perfused with the control TEA-barium solution in order to observe reversal of the effect.

The strength of the effect obtained is compared to that of a 100 μM cadmium solution. Inhibition of the potential-dependent barium current varies as a function of the doses of compounds studied and, for the most active compounds, is of the order of 49% at a concentration of 1 μM and of 83% at a concentration of 10 μM.

The results of the tests carried out on the compounds of the invention show that, in vitro, they have neuronal calcium antagonist properties and, in vivo, they have neuroprotective and anti-ischaemic properties.

These results suggest that the compounds of the invention may be used for the treatment and prevention of cerebral disorders such as those following, for example, an ischaemic attack, a cardiac or respiratory arrest, a cerebral embolism or thrombosis, for the treatment of cerebral senility, dementia following multiple infarctions, senile dementia, for example Alzheimer's disease or Pick's disease, for the treatment of olivopontocerebellar atrophy and other neurodegenerative diseases such as Huntington's chorea and amyotrophic lateral sclerosis, for the treatment of cranial or spinal trauma, for the prevention of neuronal damage following convulsive states, for the treatment of certain cancers, for the treatment of neurological damage caused by AIDS, and for the prevention and treatment of diabetic retinopathies, degeneration of the optic nerve and retinopathies associated with glaucoma, and in general for the treatment of any pathology associated with dysfunction of the neuronal calcium homeostasis.

To this end, the compounds may be provided in any all pharmaceutical form adapted for enteral or parenteral administration, in combination with suitable excipients, for example in the form of tablets, sugar-coated tablets, gelatin capsules, wafer capsules, suppositories, or drinkable or injectable solutions or suspensions, which are dosed to allow a daily administration of 1 to 1000 mg of active substance.

We claim:

1. A compound, of the formula:

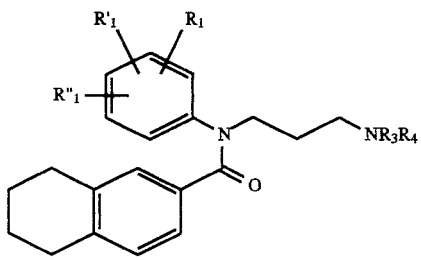

in which $R_1$ represents a hydrogen, halogen, methyl, or a $C_1$–$C_4$ alkoxy, $R'_1$ represents hydrogen or halogen;

$R''_1$ represents hydrogen or methoxy and $R_3$ and $R_4$ together form, with the nitrogen atom to which they are attached, 1,2,3,4-tetrahydroisoquinol-2-yl, 6,7-dimethoxy-1,2,3,4-tetrahydroisoquinol-2-yl, 5,8-dimethoxy-1,2,3,4-tetrahydroisoquinol-2-yl, 1,2,3,4-tetrahydro-9H-pyrido[3,4-b]indol-2-yl, 1,2,3,4-tetrahydro-9H-pyrido[4,3-b]indol-3-yl, 4,5,6,7-tetrahydrothieno[2,3-c]pyrid-6-yl, 2,3-dihydro-1H-isoindol-2-yl group, or 2,3,4,5-tetrahydro-1H-3-benzazepin-3-yl, the respective formulae of which are as follows:

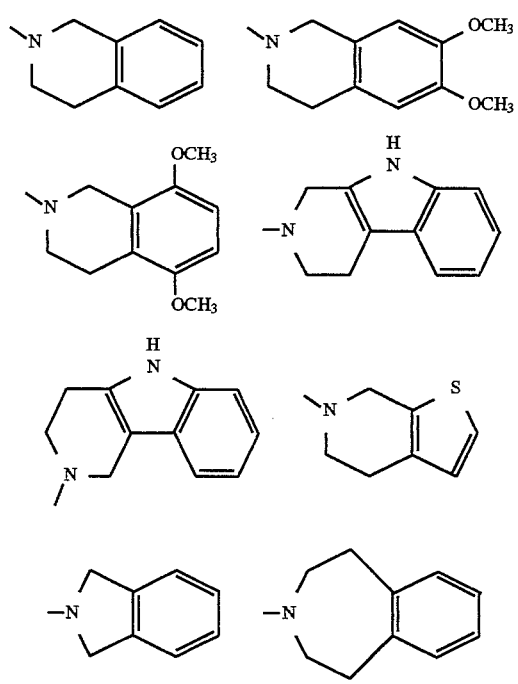

provided that, when $R_1$ is alkoxy and each of $R'_1$ and $R''_1$ is hydrogen, $R_3$ and $R_4$ do not form, with the nitrogen atom, an unsubstituted or substituted tetrahydroisoquinol-2-yl group in the form of a pure optical isomer or a mixture thereof, and in the form of a base or an acid addition salt.

2. Compound according to claim 1, wherein $R_1$ represents halogen $R'_1$ represents hydrogen or halogen $R''_1$ represents hydrogen, and $R_3$ and $R_4$ together form, with the nitrogen atom to which they are attached, 1,2,3,4-tetrahydroisoquinol-2-yl, 6,7-dimethoxy-1,2,3,4-tetrahydroisoquinol-2-yl or 5,8-dimethoxy-1,2,3,4-tetrahydroisoquinol-2-yl.

3. Pharmaceutical composition useful for the treatment and prevention of cerebral disorders comprising an effective account of a compound according to claim 1, combined with excipient.

* * * * *